United States Patent
Slate et al.

(10) Patent No.: US 9,616,173 B2
(45) Date of Patent: *Apr. 11, 2017

(54) SYSTEM AND METHOD FOR AN INJECTION USING A SYRINGE NEEDLE

(75) Inventors: John B. Slate, San Diego, CA (US); Richard J. Koerner, San Diego, CA (US); Corey M. Magers, Encinitas, CA (US); Michael W. Burk, San Marcos, CA (US)

(73) Assignee: AVANT MEDICAL CORPORATION, Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/269,750

(22) Filed: Oct. 10, 2011

(65) Prior Publication Data

US 2012/0089119 A1 Apr. 12, 2012

Related U.S. Application Data

(63) Continuation of application No. 12/178,447, filed on Jul. 23, 2008, now Pat. No. 8,052,645.

(51) Int. Cl.
*A61M 5/20* (2006.01)
*A61M 5/32* (2006.01)
*A61M 5/315* (2006.01)

(52) U.S. Cl.
CPC .............. *A61M 5/20* (2013.01); *A61M 5/326* (2013.01); *A61M 2005/206* (2013.01);
(Continued)

(58) Field of Classification Search
CPC .. A61M 2005/208; A61M 2005/31588; A61M 2205/50; A61M 2205/6045; A61M 5/20; A61M 5/326; A61M 2005/206
See application file for complete search history.

(56) References Cited

U.S. PATENT DOCUMENTS 2,701,566 A 2/1950 Krug
2,565,081 A 8/1951 Maynes
(Continued)

FOREIGN PATENT DOCUMENTS

AU 2009249027 B2 8/2014
CA 2074565 7/1992
(Continued)

OTHER PUBLICATIONS

International Search Report issued for International Application No. PCT/US09/44693 filed May 20, 2009 of Slate et al.
(Continued)

*Primary Examiner* — Theodore Stigell
(74) *Attorney, Agent, or Firm* — Marshall, Gerstein & Borun LLP

(57) ABSTRACT

An auto-injector for injecting a fluid medicament into a patient from a pre-filled syringe requires a disposable cassette that is selectively engageable with the reusable injector. The syringe is latched onto the cassette, and the cassette is then engaged with the injector. Activation of the injector causes a first motor to move the syringe so its needle is extended from a concealed position inside the cassette for injection of the medicament. A second motor on the injector is then activated to expel fluid medicament from the syringe. Then, the first motor is again activated to withdraw the syringe into the cassette for disposal of the cassette/syringe after an injection.

8 Claims, 2 Drawing Sheets

(52) U.S. Cl.
CPC .......... A61M 2005/208 (2013.01); A61M 2005/31588 (2013.01); A61M 2205/50 (2013.01); A61M 2205/6045 (2013.01)

(56) References Cited

U.S. PATENT DOCUMENTS

| | | | |
|---|---|---|---|
| 3,051,173 A | 8/1962 | Johnson et al. | |
| 3,064,650 A | 11/1962 | Lewis | |
| 3,720,211 A | 3/1973 | Kyrias | |
| 3,964,481 A | 6/1976 | Gourlandt et al. | |
| 4,108,177 A | 8/1978 | Pistor | |
| 4,276,879 A | 7/1981 | Yiournas | |
| 4,421,107 A | 12/1983 | Estes et al. | |
| 4,515,590 A | 5/1985 | Daniel | |
| 4,573,975 A | 3/1986 | Frist | |
| 4,613,328 A | 9/1986 | Boyd | |
| 4,617,016 A | 10/1986 | Blomberg | |
| 4,636,201 A | 1/1987 | Ambrose et al. | |
| 4,758,227 A | 7/1988 | Lancaster | |
| 4,787,893 A | 11/1988 | Villette | |
| 4,902,279 A | 2/1990 | Schmidtz et al. | |
| 4,986,818 A | 1/1991 | Imbert et al. | |
| 5,013,299 A | 5/1991 | Clark | |
| 5,024,616 A | 6/1991 | Ogle, II | |
| 5,034,003 A | 7/1991 | Denance | |
| 5,085,641 A | 2/1992 | Sarnoff et al. | |
| 5,092,843 A | 3/1992 | Monroe et al. | |
| 5,098,400 A | 3/1992 | Crouse et al. | |
| 5,114,404 A | 5/1992 | Paxton et al. | |
| 5,114,406 A | 5/1992 | Gabriel et al. | |
| 5,176,643 A | 1/1993 | Kramer et al. | |
| 5,221,268 A | 6/1993 | Barton et al. | |
| 5,300,029 A | 4/1994 | Denance | |
| 5,318,522 A | 6/1994 | D'Antonio | |
| 5,352,196 A | 10/1994 | Haber et al. | |
| 5,354,286 A | 10/1994 | Mesa et al. | |
| 5,354,287 A | 10/1994 | Wacks | |
| 5,425,715 A | 6/1995 | Dalling et al. | |
| 5,456,670 A | 10/1995 | Neer et al. | |
| 5,458,263 A | 10/1995 | Ciammitti | |
| 5,478,316 A | 12/1995 | Bitdinger et al. | |
| 5,540,664 A | 7/1996 | Wyrick | |
| 5,569,190 A | 10/1996 | D'Antonio | |
| 5,578,014 A | 11/1996 | Erez et al. | |
| 5,584,815 A | 12/1996 | Pawelka et al. | |
| 5,593,390 A | 1/1997 | Castellano et al. | |
| 5,599,302 A | 2/1997 | Lilley et al. | |
| 5,665,071 A | 9/1997 | Wyrick | |
| 5,681,291 A | 10/1997 | Galli | |
| 5,690,618 A | 11/1997 | Smith et al. | |
| 5,695,472 A | 12/1997 | Wyrick | |
| 5,709,662 A * | 1/1998 | Olive et al. | 604/135 |
| 5,720,729 A | 2/1998 | Kriesel | |
| 5,728,074 A | 3/1998 | Castellano et al. | |
| 5,746,714 A | 5/1998 | Salo et al. | |
| 5,779,683 A | 7/1998 | Meyer | |
| 5,807,346 A | 9/1998 | Frezza | |
| 5,843,036 A | 12/1998 | Olive et al. | |
| 5,868,711 A | 2/1999 | Kramer et al. | |
| 5,911,703 A | 6/1999 | Slate et al. | |
| 5,919,159 A | 7/1999 | Lilley et al. | |
| 5,921,963 A | 7/1999 | Erez et al. | |
| 5,957,897 A | 9/1999 | Jeffrey | |
| 6,019,745 A | 2/2000 | Gray | |
| 6,019,747 A | 2/2000 | McPhee | |
| 6,051,896 A | 4/2000 | Shibuya et al. | |
| 6,099,503 A | 8/2000 | Stradella | |
| 6,149,626 A | 11/2000 | Bachynsky et al. | |
| 6,159,184 A | 12/2000 | Perez et al. | |
| 6,171,276 B1 | 1/2001 | Lippe et al. | |
| 6,171,283 B1 | 1/2001 | Perez et al. | |
| 6,183,442 B1 | 2/2001 | Athanasiou et al. | |
| 6,203,530 B1 | 3/2001 | Stewart, Sr. | |
| 6,210,369 B1 | 4/2001 | Wilmot et al. | |
| 6,213,987 B1 | 4/2001 | Hirsch | |
| 6,241,709 B1 | 6/2001 | Bechtold et al. | |
| 6,270,479 B1 | 8/2001 | Bergens et al. | |
| 6,280,421 B1 | 8/2001 | Kirchhofer et al. | |
| 6,290,683 B1 | 9/2001 | Erez et al. | |
| 6,344,030 B1 | 2/2002 | Duchon et al. | |
| 6,344,032 B1 | 2/2002 | Perez et al. | |
| 6,371,939 B2 | 4/2002 | Bergens et al. | |
| 6,406,456 B1 | 6/2002 | Slate et al. | |
| 6,447,482 B1 | 9/2002 | Ronborg et al. | |
| 6,454,743 B1 | 9/2002 | Weber | |
| 6,520,928 B1 | 2/2003 | Junior | |
| 6,544,234 B1 | 4/2003 | Gabriel | |
| 6,547,755 B1 * | 4/2003 | Lippe et al. | 604/67 |
| 6,569,127 B1 | 5/2003 | Fago et al. | |
| 6,599,272 B1 | 7/2003 | Hjertman et al. | |
| 6,641,561 B1 | 11/2003 | Hill et al. | |
| 6,645,169 B1 | 11/2003 | Slate et al. | |
| 6,645,177 B1 | 11/2003 | Shearn | |
| 6,648,858 B2 | 11/2003 | Asbaghi | |
| 6,652,483 B2 | 11/2003 | State et al. | |
| 6,656,163 B1 | 12/2003 | Marshall et al. | |
| 6,656,164 B1 | 12/2003 | Smith | |
| 6,669,664 B2 | 12/2003 | Slate et al. | |
| 6,692,469 B1 | 2/2004 | Weekes et al. | |
| 6,743,202 B2 | 6/2004 | Hirschman | |
| 6,746,427 B2 | 6/2004 | Duchon et al. | |
| 6,752,787 B1 | 6/2004 | Causey, III et al. | |
| 6,767,336 B1 | 7/2004 | Kaplan | |
| 6,770,052 B2 | 8/2004 | Hill et al. | |
| 6,796,957 B2 | 9/2004 | Carpenter et al. | |
| 6,805,686 B1 | 10/2004 | Fathallah et al. | |
| 6,808,507 B2 | 10/2004 | Roser | |
| 6,835,193 B2 | 12/2004 | Epstein et al. | |
| 6,854,620 B2 | 2/2005 | Ramey | |
| 6,890,319 B1 | 5/2005 | Crocker | |
| 6,932,793 B1 | 8/2005 | Marshall et al. | |
| 6,979,316 B1 | 12/2005 | Rubin et al. | |
| 7,008,399 B2 | 3/2006 | Larsen et al. | |
| 7,011,649 B2 | 3/2006 | De La Serna et al. | |
| 7,025,774 B2 | 4/2006 | Freeman | |
| 7,041,085 B2 | 5/2006 | Perez et al. | |
| 7,066,909 B1 | 6/2006 | Peter et al. | |
| 7,094,230 B2 | 8/2006 | Flaherty et al. | |
| 7,104,400 B2 | 9/2006 | Kiehne | |
| 7,118,553 B2 | 10/2006 | Scherer | |
| 7,226,450 B2 | 6/2007 | Athanasiou et al. | |
| 7,255,684 B2 | 8/2007 | Zubry | |
| 7,273,469 B1 | 9/2007 | Chan et al. | |
| 7,290,573 B2 | 11/2007 | Py et al. | |
| 7,297,135 B2 | 11/2007 | Jeffrey | |
| 7,297,136 B2 | 11/2007 | Wyrick | |
| 7,357,790 B2 | 4/2008 | Hommann et al. | |
| 7,361,160 B2 | 4/2008 | Hommann et al. | |
| 7,370,759 B2 | 5/2008 | Hommann | |
| 7,381,201 B2 | 6/2008 | Gilbert et al. | |
| 7,442,185 B2 | 10/2008 | Amark et al. | |
| 7,449,012 B2 | 11/2008 | Young et al. | |
| 7,500,963 B2 | 3/2009 | Westbye et al. | |
| 7,500,966 B2 | 3/2009 | Hommann | |
| 7,553,294 B2 | 6/2009 | Lazzaro | |
| 7,597,685 B2 | 10/2009 | Olson | |
| 7,635,348 B2 | 12/2009 | Raven et al. | |
| 7,635,350 B2 | 12/2009 | Scherer | |
| 7,648,483 B2 | 1/2010 | Edwards et al. | |
| 7,654,987 B2 | 2/2010 | Hommann et al. | |
| 7,686,789 B2 | 3/2010 | Nemoto | |
| 7,731,686 B2 | 6/2010 | Edwards et al. | |
| 7,749,195 B2 | 7/2010 | Hommann | |
| 7,760,099 B2 | 7/2010 | Knight | |
| 7,785,292 B2 | 8/2010 | Harrison | |
| 7,828,776 B2 | 11/2010 | Nemoto | |
| 7,887,513 B2 | 2/2011 | Nemoto | |
| 7,901,377 B1 | 3/2011 | Harrison et al. | |
| 7,918,823 B2 | 4/2011 | Edwards et al. | |
| 7,922,695 B2 | 4/2011 | Wiegel et al. | |
| 7,976,499 B2 | 7/2011 | Grunhut et al. | |
| 8,012,125 B1 | 9/2011 | Fago et al. | |
| 8,016,797 B2 | 9/2011 | Gratwohl et al. | |
| 8,043,262 B2 | 10/2011 | Streit et al. | |

(56) References Cited

U.S. PATENT DOCUMENTS

| | | | |
|---|---|---|---|
| 8,052,645 B2 * | 11/2011 | Slate et al. | 604/154 |
| 8,141,417 B2 | 3/2012 | Gibson | |
| 8,177,749 B2 * | 5/2012 | Slate et al. | 604/131 |
| 8,298,171 B2 | 10/2012 | Ishikawa | |
| 8,337,472 B2 | 12/2012 | Edginton | |
| 2001/0005781 A1 * | 6/2001 | Bergens et al. | 604/208 |
| 2001/0047153 A1 | 11/2001 | Trocki et al. | |
| 2003/0036725 A1 | 2/2003 | Lavi et al. | |
| 2003/0105430 A1 | 6/2003 | Lavi et al. | |
| 2003/0236502 A1 | 12/2003 | De La Serna et al. | |
| 2004/0039336 A1 | 2/2004 | Amark et al. | |
| 2004/0054327 A1 | 3/2004 | Gillespie | |
| 2004/0068266 A1 | 4/2004 | Delmotte | |
| 2004/0116861 A1 | 6/2004 | Trocki et al. | |
| 2004/0129803 A1 | 7/2004 | Dolder et al. | |
| 2004/0133154 A1 | 7/2004 | Flaherty et al. | |
| 2004/0133162 A1 | 7/2004 | Trocki et al. | |
| 2004/0153008 A1 | 8/2004 | Sharf et al. | |
| 2004/0225262 A1 | 11/2004 | Fathallah et al. | |
| 2005/0020979 A1 | 1/2005 | Westbye et al. | |
| 2005/0027255 A1 | 2/2005 | Lavi et al. | |
| 2005/0033242 A1 | 2/2005 | Perez et al. | |
| 2005/0049561 A1 | 3/2005 | Hommann et al. | |
| 2005/0054987 A1 | 3/2005 | Perez et al. | |
| 2005/0080377 A1 | 4/2005 | Sadowski et al. | |
| 2005/0165404 A1 | 7/2005 | Miller | |
| 2005/0171476 A1 | 8/2005 | Judson et al. | |
| 2005/0171477 A1 * | 8/2005 | Rubin et al. | 604/156 |
| 2005/0197650 A1 | 9/2005 | Sugimoto et al. | |
| 2005/0203466 A1 | 9/2005 | Hommann et al. | |
| 2005/0209569 A1 | 9/2005 | Ishikawa et al. | |
| 2005/0261693 A1 | 11/2005 | Miller et al. | |
| 2005/0277885 A1 * | 12/2005 | Scherer | 604/136 |
| 2006/0030819 A1 | 2/2006 | Young et al. | |
| 2006/0157064 A1 | 7/2006 | Davison et al. | |
| 2006/0251646 A1 | 11/2006 | Utku | |
| 2006/0270985 A1 | 11/2006 | Hommann et al. | |
| 2007/0021720 A1 | 1/2007 | Guillermo | |
| 2007/0027430 A1 | 2/2007 | Hommann | |
| 2007/0066938 A1 | 3/2007 | Iio et al. | |
| 2007/0100281 A1 | 5/2007 | Morris et al. | |
| 2007/0112301 A1 | 5/2007 | Preuthun et al. | |
| 2007/0112310 A1 | 5/2007 | Lavi et al. | |
| 2007/0118081 A1 | 5/2007 | Daily et al. | |
| 2007/0135767 A1 | 6/2007 | Gillespie et al. | |
| 2007/0142787 A1 | 6/2007 | Scherer | |
| 2007/0149925 A1 | 6/2007 | Edwards et al. | |
| 2007/0167920 A1 | 7/2007 | Hommann | |
| 2007/0173770 A1 | 7/2007 | Stamp | |
| 2007/0197954 A1 | 8/2007 | Keenan | |
| 2007/0197968 A1 | 8/2007 | Pongpairochana et al. | |
| 2007/0219498 A1 | 9/2007 | Malone et al. | |
| 2007/0233001 A1 | 10/2007 | Burroughs et al. | |
| 2007/0239114 A1 | 10/2007 | Edwards et al. | |
| 2007/0265568 A1 | 11/2007 | Tsals et al. | |
| 2008/0039795 A1 * | 2/2008 | Slate et al. | 604/136 |
| 2008/0051711 A1 | 2/2008 | Mounce et al. | |
| 2008/0051714 A1 | 2/2008 | Moberg et al. | |
| 2008/0051715 A1 | 2/2008 | Young et al. | |
| 2008/0132841 A1 | 6/2008 | Chiwanga et al. | |
| 2008/0140007 A1 | 6/2008 | Glynn | |
| 2008/0262434 A1 | 10/2008 | Vaillancourt | |
| 2008/0312602 A1 | 12/2008 | Barrow-Williams et al. | |
| 2009/0018494 A1 | 1/2009 | Nemoto et al. | |
| 2009/0018505 A1 | 1/2009 | Arguedas et al. | |
| 2009/0024112 A1 | 1/2009 | Edwards et al. | |
| 2009/0043253 A1 | 2/2009 | Podaima et al. | |
| 2009/0149744 A1 | 6/2009 | Nemoto et al. | |
| 2009/0270672 A1 | 10/2009 | Fago | |
| 2009/0292246 A1 | 11/2009 | Slate et al. | |
| 2009/0312705 A1 | 12/2009 | Grunhut et al. | |
| 2009/0322545 A1 | 12/2009 | Gibson | |
| 2010/0016793 A1 | 1/2010 | Jennings et al. | |
| 2010/0016795 A1 | 1/2010 | McLoughlin | |
| 2010/0021456 A1 | 1/2010 | Miossec et al. | |
| 2010/0022955 A1 | 1/2010 | Slate et al. | |
| 2010/0036318 A1 | 2/2010 | Raday et al. | |
| 2010/0152655 A1 | 6/2010 | Stamp | |
| 2010/0152659 A1 | 6/2010 | Streit et al. | |
| 2010/0160894 A1 | 6/2010 | Julian et al. | |
| 2010/0198060 A1 | 8/2010 | Fago et al. | |
| 2010/0268170 A1 | 10/2010 | Carrel et al. | |
| 2010/0312195 A1 | 12/2010 | Johansen et al. | |
| 2011/0004165 A1 | 1/2011 | Iio et al. | |
| 2011/0023281 A1 | 2/2011 | Schraga | |
| 2011/0044998 A1 | 2/2011 | Bedian et al. | |
| 2011/0047153 A1 | 2/2011 | Betz | |
| 2011/0097229 A1 | 4/2011 | Cauley, III et al. | |
| 2011/0098655 A1 | 4/2011 | Jennings et al. | |
| 2011/0137286 A1 | 6/2011 | Mudd et al. | |
| 2011/0144594 A1 | 6/2011 | Sund et al. | |
| 2011/0152781 A1 | 6/2011 | Brunnberg et al. | |
| 2011/0160580 A1 | 6/2011 | Perkins et al. | |
| 2011/0166512 A1 | 7/2011 | Both et al. | |
| 2011/0184383 A1 | 7/2011 | Hasegawa | |
| 2011/0190693 A1 | 8/2011 | Takatsuka et al. | |
| 2011/0190702 A1 | 8/2011 | Stumber | |
| 2011/0196339 A1 | 8/2011 | Hirschel et al. | |
| 2011/0202011 A1 | 8/2011 | Wozencroft | |
| 2011/0213315 A1 | 9/2011 | Sweeney et al. | |
| 2011/0224616 A1 | 9/2011 | Slate et al. | |
| 2011/0224620 A1 | 9/2011 | Johansen et al. | |
| 2011/0224621 A1 | 9/2011 | Johansen et al. | |
| 2011/0230833 A1 | 9/2011 | Landman et al. | |
| 2011/0245761 A1 | 10/2011 | Jennings et al. | |
| 2011/0257596 A1 | 10/2011 | Gaudet | |
| 2011/0264046 A1 | 10/2011 | Nyholm et al. | |
| 2012/0035472 A1 | 2/2012 | Bruce et al. | |
| 2012/0035538 A1 | 2/2012 | Elmen et al. | |
| 2012/0059319 A1 | 3/2012 | Segal | |
| 2012/0089119 A1 | 4/2012 | Slate et al. | |
| 2012/0101439 A9 | 4/2012 | Slate et al. | |
| 2012/0238961 A1 | 9/2012 | Julian et al. | |
| 2012/0265142 A1 | 10/2012 | Slate et al. | |
| 2012/0323176 A1 | 12/2012 | Watanabe et al. | |
| 2013/0131601 A1 | 5/2013 | Pommereau et al. | |
| 2015/0045729 A1 | 2/2015 | Denzer et al. | |
| 2016/0022914 A1 | 1/2016 | Mounce et al. | |
| 2016/0120751 A1 | 5/2016 | Mounce et al. | |

FOREIGN PATENT DOCUMENTS

| | | | |
|---|---|---|---|
| ES | 2121536 A1 | 11/1998 | |
| FR | 2390175 | 4/1976 | |
| FR | 2592307 A1 | 7/1987 | |
| FR | 2622457 A1 | 5/1989 | |
| FR | 2716375 A1 | 8/1995 | |
| JP | S63139563 A | 6/1988 | |
| JP | H07185000 A | 4/1995 | |
| JP | H07503384 A | 4/1995 | |
| JP | H07185000 A | 7/1995 | |
| JP | 2001518366 A | 10/2001 | |
| JP | 2002543931 A | 12/2002 | |
| JP | 2003220142 A | 8/2003 | |
| JP | 20020531228 A | 8/2004 | |
| JP | 2005514082 A | 5/2005 | |
| JP | 2006507061 A | 3/2006 | |
| JP | 2006528040 A | 12/2006 | |
| JP | 2007-500561 A | 1/2007 | |
| JP | 2007111518 A | 5/2007 | |
| JP | 2007529243 A | 10/2007 | |
| JP | 2008508961 A | 3/2008 | |
| JP | 2010511414 A | 4/2010 | |
| JP | 2015186876 A | 10/2015 | |
| WO | 8606967 A1 | 12/1986 | |
| WO | 8703494 A1 | 6/1987 | |
| WO | 8707160 A1 | 12/1987 | |
| WO | 9118634 A1 | 12/1991 | |
| WO | 9206725 A1 | 4/1992 | |
| WO | 9208506 A1 | 5/1992 | |
| WO | 9221392 A1 | 12/1992 | |
| WO | 9302728 A1 | 2/1993 | |
| WO | 9313817 A1 | 7/1993 | |
| WO | 9324160 A1 | 12/1993 | |

(56) References Cited

FOREIGN PATENT DOCUMENTS

| | | |
|---|---|---|
| WO | 9325256 A1 | 12/1993 |
| WO | 9406494 A1 | 3/1994 |
| WO | 9521645 A1 | 8/1995 |
| WO | 9525555 A1 | 9/1995 |
| WO | 9531235 A1 | 11/1995 |
| WO | 9534333 A2 | 12/1995 |
| WO | 9600594 A1 | 1/1996 |
| WO | 9621482 A2 | 7/1996 |
| WO | 9626754 A2 | 9/1996 |
| WO | 9638190 A1 | 12/1996 |
| WO | 9707839 A1 | 3/1997 |
| WO | 9731665 A1 | 9/1997 |
| WO | 9813077 A2 | 4/1998 |
| WO | 9817332 A2 | 4/1998 |
| WO | 9821408 A1 | 5/1998 |
| WO | 9917823 A1 | 4/1999 |
| WO | 9920327 A2 | 4/1999 |
| WO | 9921600 A2 | 5/1999 |
| WO | 0002605 A1 | 1/2000 |
| WO | 0009186 A2 | 2/2000 |
| WO | 0024441 A1 | 5/2000 |
| WO | 0025846 A2 | 5/2000 |
| WO | 0100261 A1 | 1/2001 |
| WO | 0137903 A2 | 5/2001 |
| WO | 0141835 A2 | 6/2001 |
| WO | 0189634 A2 | 11/2001 |
| WO | 0207812 A2 | 1/2002 |
| WO | 0249691 A2 | 6/2002 |
| WO | 02092153 A2 | 11/2002 |
| WO | 03006099 A1 | 1/2003 |
| WO | 03008023 A1 | 1/2003 |
| WO | 03047663 A2 | 6/2003 |
| WO | 03090509 A2 | 11/2003 |
| WO | 03103749 A2 | 12/2003 |
| WO | 2004069303 A2 | 8/2004 |
| WO | 2004108193 A1 | 12/2004 |
| WO | 2005053771 A2 | 6/2005 |
| WO | 2005070481 A1 | 8/2005 |
| WO | 2005079440 A2 | 9/2005 |
| WO | 2005089831 | 9/2005 |
| WO | 2005094923 A1 | 10/2005 |
| WO | 2006015501 A1 | 2/2006 |
| WO | 2006017732 A2 | 2/2006 |
| WO | 2006020609 A1 | 2/2006 |
| WO | 2006062788 A2 | 6/2006 |
| WO | 2006063015 A2 | 6/2006 |
| WO | 2006084821 A2 | 8/2006 |
| WO | 2006086774 A2 | 8/2006 |
| WO | 2007002053 A2 | 1/2007 |
| WO | 2007044980 A2 | 4/2007 |
| WO | 2007047200 A1 | 4/2007 |
| WO | 2007053779 A2 | 5/2007 |
| WO | 2007075677 A2 | 7/2007 |
| WO | 2007099044 A1 | 9/2007 |
| WO | 2007126851 A2 | 11/2007 |
| WO | 2007138299 A1 | 12/2007 |
| WO | 2007138313 A1 | 12/2007 |
| WO | 2007140610 A1 | 12/2007 |
| WO | 2008021776 A2 | 2/2008 |
| WO | 2008024810 A2 | 2/2008 |
| WO | 2008048750 A2 | 4/2008 |
| WO | 2008064092 A2 | 5/2008 |
| WO | 2008075033 A1 | 6/2008 |
| WO | 2008083313 A2 | 7/2008 |
| WO | 2008093063 A2 | 8/2008 |
| WO | 2008094984 A2 | 8/2008 |
| WO | 2008095124 A1 | 8/2008 |
| WO | 2008107670 A2 | 9/2008 |
| WO | 2008139458 A2 | 11/2008 |
| WO | 2008139460 A2 | 11/2008 |
| WO | 2008146021 A1 | 12/2008 |
| WO | 2009006725 A1 | 1/2009 |
| WO | 2009019437 A1 | 2/2009 |
| WO | 2009097325 A1 | 8/2009 |
| WO | 2009125879 A1 | 10/2009 |
| WO | 2009143255 A1 | 11/2009 |
| WO | 2010023481 A1 | 3/2010 |
| WO | 2010026414 A1 | 3/2010 |
| WO | 2010076275 A1 | 7/2010 |
| WO | 2010091133 A2 | 8/2010 |
| WO | 2010100213 A1 | 9/2010 |
| WO | 2010127449 A1 | 11/2010 |
| WO | 2011057065 A1 | 5/2011 |
| WO | 2012000871 A1 | 1/2012 |
| WO | 2012000940 A2 | 1/2012 |
| WO | 2012145685 A1 | 10/2012 |
| WO | 2012164389 A2 | 12/2012 |
| WO | 2012164394 A2 | 12/2012 |
| WO | 2012164397 | 12/2012 |
| WO | 2013001378 A1 | 1/2013 |
| WO | 2013034984 | 3/2013 |
| WO | 2013034986 | 3/2013 |
| WO | 2013065055 A1 | 5/2013 |
| WO | 2014143815 A2 | 9/2014 |
| WO | 2014144096 A1 | 9/2014 |

OTHER PUBLICATIONS

Written Opinion of the International Searching Authority issued for International Application No. PCT/US09/44693 filed May 20, 2009 of Slate et al.
International Preliminary Report on Patentability of the International Searching Authority issued for International Application No. PCT/US09/44693 filed May 20, 2009 of Slate et al.
Notice of Allowance dated Apr. 6, 2011 issued in co-pending U.S. Appl. No. 12/178,447, filed Jul. 23, 2008 of Slate et al.
Notice of Allowance dated Jun. 24, 2011 issued in co-pending U.S. Appl. No. 12/178,447, filed Jul. 23, 2008 of Slate et al.
Office Action dated Oct. 15, 2009 issued in co-pending U.S. Appl. No. 12/178,447, filed Jul. 23, 2008 of Slate et al.
Office Action dated Mar. 30, 2010 issued in co-pending U.S. Appl. No. 12/178,447, filed Jul. 23, 2008 of Slate et al.
Office Action dated Dec. 22, 2010 issued in co-pending U.S. Appl. No. 12/178,447, filed Jul. 23, 2008 of Slate et al.
Notice of Allowance dated Oct. 3, 2011 issued in co-pending U.S. Appl. No. 12/123,888, filed May 20, 2008 of Slate et al.
Notice of Allowance dated Jan. 12, 2012 issued in co-pending U.S. Appl. No. 12/123,888, filed May 20, 2008 of Slate et al.
Office Action dated Oct. 5, 2009 issued in co-pending U.S. Appl. No. 12/123,888, filed May 20, 2008 of Slate et al.
Office Action dated Apr. 8, 2010 issued in co-pending U.S. Appl. No. 12/123,888, filed May 20, 2008 of Slate et al.
Office Action dated Dec. 22, 2010 issued in co-pending U.S. Appl. No. 12/123,888, filed May 20, 2008 of Slate et al.
Office Action dated Jun. 8, 2011 issued in co-pending U.S. Appl. No. 12/123,888, filed May 20, 2008 of Slate et al.
U.S. Appl. No. 13/454,531, filed Apr. 24, 2012, entitled, "Cassette for a Hidden Injection Needle," of Slate et al.
U.S. Appl. No. 12/993,163, filed May 27, 2011, entitled, "Autoinjector System," of Slate et al.
"Office Action issued in related Australian Patent Application No. 2009 249027", Jul. 24, 2013, Publisher: IP Australia, Published in: AU.
Martin Schindler, "Office Action issued in related European Patent Application No. EP 09 75 1483", Aug. 1, 2013, Publisher: EPO, Published in: EP.
"Office Action issued in related Japanese Patent Application No. JP 2011-510683", Jul. 30, 2013, Publisher: JPO, Published in: JP.
"Office Action issued in related U.S. Appl. No. 12/993,163", Sep. 3, 2013, Publisher: USPTO, Published in: US.
Officer: Lee W. Young, "International Search Report and Written Opinion in related International Application No. PCT/US2012/34535", Aug. 17, 2012, Publisher: PCT, Published in: US.
Officer(s): Athina Nickitas-Etienne and Lee W. Young, "International Preliminary Report on Patentability and Written Opinion of the ISA issued in related International Application No. PCT/US2012/034535", Oct. 31, 2013, Publisher: PCT, Published in: CH.
"Office Action issued in related U.S. Appl. No. 12/454,531", Dec. 28, 2012, Publisher: USPTO, Published in: US.

(56) References Cited

OTHER PUBLICATIONS

"Office Action issued in related U.S. Appl. No. 12/454,531", Sep. 13, 2013, Publisher: USPTO, Published in: US.
"Non-Final Office Action issued in related U.S. Appl. No. 12/993,163", Sep. 11, 2014, Publisher: USPTO.
"Notice of Acceptance issued in related Australian Patent Application No. 2009249027", Aug. 7, 2014, Publisher: IPA.
"Office Action issued in related European Patent Application No. EP 09 751 483.0", May 14, 2014, Publisher: EPO.
"Office Action issued in related Japanese Patent Application No. JP 2011-510683", Jun. 30, 2014, Publisher: JPO.
"Office Action issued in related Mexican Patent Application No. MX/a/2010/012691", Feb. 10, 2014, Publisher: Ilnstituto Mexicano de la Propiedad Industrial.
"Non-Final Office Action issued in related U.S. Appl. No. 12/993,163", Dec. 27, 2013, Publisher: USPTO.
"Related U.S. Appl. No. 14/112,479", Oct. 17, 2013, Publisher: USPTO.
"Non-Final Office Action issued in related U.S. Appl. No. 13/454,531", Oct. 7, 2014, Publisher: USPTO.
"Notice of Allowance issued in related U.S. Appl. No. 13/454,531", Apr. 3, 2014, Publisher: USPTO.
"Non-Final Office Action issued in related U.S. Appl. No. 13/454,531", Dec. 28, 2012, Publisher: USPTO.
"Final Office Action issued in related U.S. Appl. No. 13/454,531", Sep. 13, 2013, Publisher: USPTO.
"International Search Report and Written Opinion issued in related International Application No. PCT/US2014/027950", Oct. 7, 2014, Publisher: ISA US.
"Related International Patent Application No. PCT/US2014/027950", Mar. 14, 2014, Publisher: PCT, Published in: US.
"Related International Patent Application No. PCT/US2014/028363", Mar. 14, 2014.
"International Search Report and Written Opinion issued in related International Application No. PCT/US2014/028363", Aug. 18, 2014, Publisher: ISA US.
"Office Action, Dated Jan. 5, 2015, issued in related Japanese Application JP2014-021052 (counterpart to U.S. Appl. No. 12/123,888)".
Jose Enrique Cazares Avila, "Office Action," dated Sep. 24, 2014, issued in Mexican Patent Application No. MX/a/2010/012691, which is the counterpart to related copending U.S. Appl. No. 12/993,163.
"Final Office Action," dated Apr. 20, 2015, issued in related Japanese Patent Application No. JP 2014-021052 (counterpart to related U.S. Appl. No. 12/993,163).
"Non-Final Office Action," dated Apr. 21, 2015, issued in related U.S. Appl. No. 12/454,531.
"Non-Final Office Action," dated May 8, 2015, issued in related U.S. Appl. No. 12/993,163.
"Office Action," dated Apr. 10, 2015, issued in related European Patent Application No. EP 09 75 1483 (counterpart to related U.S. Appl. No. 12/993,163).
"First Examination Report", dated Jun. 4, 2015, issued in Related Canadian Patent Application No. 2,724,641 (counterpart to related U.S. Appl. No. 12/993,163).
"Final Office Action", dated Jun. 1, 2015, issued in Related Japanese Patent Application No. 2011-510683 (counterpart to related U.S. Appl. No. 12/993,163).
"Extended European Search Report", dated Jul. 16, 2015, issued in Related European Patent Application No. 12774589 (counterpart to related U.S. Appl. No. 14/112,479).
"Notice of Allowance", dated Oct. 5, 2015, issued in related U.S. Appl. No. 13/454,531.
"EP Office Action" issued in European Patent Application No. 09 751 483.0, dated Nov. 16, 2015 (Foreign counterpart to related U.S. Appl. No. 12/123,888).
"Office Action" dated Nov. 23, 2015, issued in Canadian Application No. 2,833,748 (Foreign counterpart to related U.S. Appl. No. 14/112,479).
"Office Action" issued in Japanese Patent Application No. 2014-506591 on Jan. 4, 2016 (Foreign counterpart to related U.S. Appl. No. 14/112,479).
"Notice of Allowance", issued in Japanese Application No. 2011-510683 (Foreign counterpart of related U.S. Appl. No. 12/993,163), Oct. 5, 2015.
"Notice of Allowance", issued in Japanese Continuation Application No. 2014-021052 (Foreign counterpart of related U.S. Appl. No. 12/993,163), Aug. 24, 2015.
"Final Office Action" issued in related U.S. Appl. No. 12/993,163, dated Feb. 22, 2016.
"First Examination Report" issued in Australian Patent Application No. 2012245231, dated Oct. 19, 2015 (Foreign counterpart to related U.S. Appl. No. 14/112,479).
"NonFinal Office Action" issued in related U.S. Appl. No. 13/454,531, dated Mar. 17, 2016.
"Office Action" issued in related Taiwan Patent application No. 103109475, dated Aug. 26, 2016.
"Office Action" issued in related Australian Patent Application No. 2014268140, dated Sep. 2, 2016.
"Office Action" issued in related Canadian Patent Application No. 2833748, dated Aug. 12, 2016.
"Office Action" issued in related European Patent Application No. 09751483.0, dated Aug. 1, 2016.
"Office Action" issued in related Japanese Patent Application No. 2015-186876, dated Jul. 15, 2016.
"Office Action" issued in related Australian Patent Application No. 2014268139, dated Jul. 19, 2016.
Office Action: issued in related Australian Patent Application No. 2014268140, dated Jul. 22, 2016.
"Office Action" issued in related Australian Patent Application No. 201224523, dated Jul. 5, 2016.
"Non Final Office Action" dated Jul. 28, 2016 in related U.S. Appl. No. 12/993,163.
"Office Action" dated Jul. 29, 2016 in related U.S. Appl. No. 14/112,479.
Authorized Officer: Yukari Nakamura, "International Preliminary Report on Patentability" issued in related PCT application No. PCT/US2014/027950, dated Jun. 15, 2015.
Authorized Officer: Simin Baharlou, "International Preliminary Report on Patentability" issued in related International Application No. PCT/US2014/028363, dated Sep. 15, 2015.
"Notice of Allowance" issued in related Japanese Patent Application No. 2014021052, dated Aug. 24, 2015.
"Notice of Allowance" issued in related Japanese Patent Application No. 2011510683, dated Oct. 5, 2015.
"Notice of Allowance" issued in related U.S. Appl. No. 12/123,888, Jan. 12, 2012.
"Office Action" issued in related Japanese Patent Application No. 2014-506591, dated Jan. 4, 2016.
"Office Action", dated Nov. 23, 2015, issued in Canadian Application No. 2,833,748 (Foreign counterpart to U.S. Appl. No. 14/112,479).
"Notice of Allowance", dated Apr. 6, 2011, issued in parent U.S. Appl. No. 12/178,447.
Related unpublished U.S. Appl. No. 29/548,507.
Related unpublished U.S. Appl. No. 29/548,508.
"Office Action" issued in related Taiwan Patent Application No. 103109332, dated Aug. 22, 2016.
"Notice of Allowance" issued in related Japanese Patent Application No. 2014-506591, dated Oct. 3, 2016.
"Office Action" issued in related U.S. Appl. No. 12/123,888, dated Oct. 5, 2009.
"Final Office Action" issued in related U.S. Appl. No. 12/123,888, dated Apr. 8, 2010.
"Office Action" issued in related U.S. Appl. No. 12/123,888, dated Dec. 22, 2010.
"Office Action" issued in parent U.S. Appl. No. 12/178,447, dated Oct. 15, 2009.
"Office Action" issued in parent U.S. Appl. No. 12/178,447, dated Dec. 22, 2010.
"Final Office Action" issued in parent U.S. Appl. No. 12/178,447, dated Mar. 30, 2010.

(56) References Cited

OTHER PUBLICATIONS

"Notice of Allowance" issued in related U.S. Appl. No. 12/123,888, Oct. 3, 2011.
"Notice of Allowance", dated Jun. 24, 2011, issued in parent U.S. Appl. No. 12/178,447.

* cited by examiner

SYSTEM AND METHOD FOR AN INJECTION USING A SYRINGE NEEDLE

RELATED APPLICATION

This application is a continuation of co-pending U.S. application Ser. No. 12/178,447, filed on Jul. 23, 2008. The entire disclosure of the application is incorporated herein by reference.

FIELD OF THE INVENTION

The present invention pertains generally to systems and methods for injecting fluid medicaments into a patient from a syringe. More particularly, the present invention pertains to auto-injectors that conceal the injection needle of a hypodermic syringe before, and after an injection. The present invention is particularly, but not exclusively, useful as a system and method that employs a bifurcated drive mechanism wherein one motor moves the entire syringe for an injection, and another motor moves the syringe plunger for expelling a fluid medicament from the syringe.

BACKGROUND OF THE INVENTION

In order to inject a fluid medicament into a patient when using a hypodermic syringe, three separate and distinct tasks must be performed. These are: 1) insertion of the needle into the patient; 2) injection of the fluid medicament from the syringe into the patient; and 3) withdrawal of the needle after the injection has been completed. For each task, the magnitude and direction of forces on the syringe, as well as the location of their application, are different from the other tasks. For instance, compare the task of inserting the needle, with the task of injecting the fluid medicament. Insertion of the needle requires that only minimal forces be applied on the syringe, and that they be applied for only a very short period of time. On the other hand, injection of the medicament requires a much greater force be applied. Further, this force must be applied on the plunger of the syringe for what will typically be a relatively longer period of time. In comparison with both of these tasks, needle withdrawal requires the application of a force in the opposite direction. These, and other similar considerations, become important when the injection process is to be automated.

Springs for generating forces on a syringe in an automated process have been used heretofore for various purposes. A characteristic of springs, however, is that the magnitude and direction of a spring force are not variable. Consequently, springs do not lend themselves for so-called "multi-tasking" operations. This is particularly so where precise control over a syringe injection operation is required, and different magnitude forces are sequentially required in the same direction (e.g. needle insertion and medicament injection).

In addition to the mechanical considerations mentioned above, the design of an auto-injector also requires "user-friendly" considerations. In particular, it is desirable that the injection needle of a syringe be operationally concealed from the view of a user. Preferably, this concealment can be maintained before, during and after an injection procedure. Further, it is desirable that operation of the syringe be limited to only those times when the syringe is properly positioned for an injection.

In light of the above, it is an object of the present invention to provide a two-motor device for performing the injection of a fluid medicament into a patient wherein each motor generates different forces on a hypodermic syringe for different purposes. Another object of the present invention is to provide a reusable injector that can be operationally engaged with a disposable, pre-filled syringe. Still another object of the present invention is to provide an auto-injector system wherein the needle of a pre-filled syringe is operationally concealed and the system is operable only when the injector is properly positioned against the skin of a patient for an injection. Another object of the present invention is to provide a system and a method for automatically injecting a fluid medicament from a pre-filled syringe that is relatively simple to manufacture, is easy to use and is comparatively cost effective.

SUMMARY OF THE INVENTION

In accordance with the present invention an autoinjector system includes a disposable cassette that operates in combination with a reusable injector. Prior to an engagement of the cassette with the injector, however, a pre-filled syringe is mounted and latched onto the cassette. When latched, the syringe is held on the cassette in a so-called "home position". For the present invention, this pre-filled syringe may be of any type syringe wellknown in the pertinent art that has a fluid chamber with an injection needle at its distal end, and a plunger that can be advanced into the fluid chamber. When the cassette, with syringe, is engaged with the injector, the system is ready for use.

Operation of the system of the present invention requires two separate motors that are individually mounted on the injector. Though they are mechanically independent of each other, the respective operations of these two motors must be coordinated. Specifically, a first motor is used to effect movements of the entire syringe assembly (i.e. syringe chamber, injection needle and plunger are all moved together). On the other hand, a second motor is employed to advance the plunger into the fluid chamber for performing an injection of a fluid medicament.

In a duty cycle of the system, the first motor moves a drive rod into engagement with the syringe. With this engagement, the drive rod also releases the latch that otherwise holds the syringe in its "home position." After the syringe has been released, the first motor then advances the syringe in a distal direction on the cassette. This movement inserts the injection needle into a patient. Further, the first motor can be used to abruptly stop the needle when a specified needle depth has been achieved. The first motor can then be used to help stabilize the needle during an injection of the medical medicament from the syringe.

As mentioned above, the injection of medical medicament from the syringe is accomplished using the second motor. In detail, once the needle has been properly inserted into the patient, the second motor moves a pusher to urge against the plunger of the syringe to advance the plunger into the fluid chamber of the syringe. Importantly, the second motor can be programmed to advance the plunger into the fluid chamber at a predetermined rate(s) for compliance with an injection protocol.

After the injection has been completed, the second motor withdraws the pusher. The first motor is then used again. Specifically, the first motor is now used to withdraw the injection needle from the patient, and to return the syringe to its "home position" on the cassette, where it is re-latched onto the cassette. The cassette can then be removed from the injector and discarded.

In order to control the concerted operations of the first and second motors, the system includes a microcomputer that is mounted on the injector. Importantly, the microcomputer operates the motors with different forces, and at different speeds for different purposes. More specifically, the first motor must operate quickly to insert the needle (e.g. 0.1 to 1 m/s), but it does not require much force to do so. Similarly, needle withdrawal by the first motor requires a minimal force. Unlike the first motor, however, the second motor will typically be required to generate greater forces for the injection of fluid medicament. And, accordingly, it will also typically operate at slower speeds. Further, and most importantly, different injections (i.e. advancements of the syringe plunger by the second motor) may require different injection rates. Thus, the second motor requires speed control provided by the microcomputer.

Together with the components mentioned above, the system of the present invention may, optionally, employ a capacitance skin sensor of a type well known in the pertinent art. If used, such a sensor will allow the user to ascertain whether the system has been properly positioned for an injection. In detail, a metal foil is positioned at the extreme distal end of the injector to establish a capacitance signal whenever the foil is in contact with a skin surface of the patient. The function of this signal is actually two-fold. First, it can be used to prevent initial operation, if the system is not properly positioned. And, second, it can be used to interrupt operation of the system, if it becomes improperly positioned during an injection.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
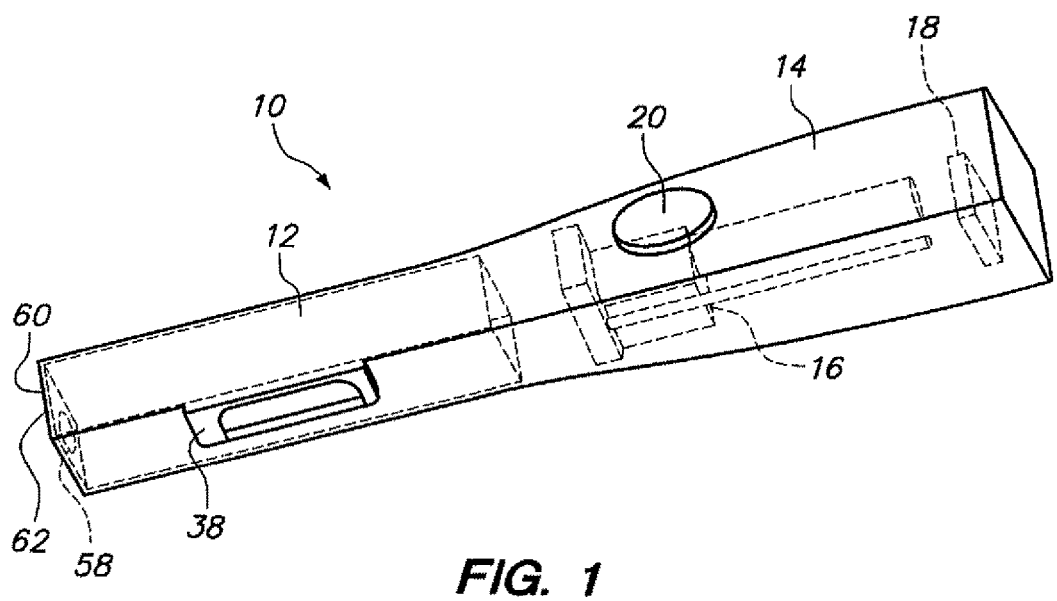
FIG. 1 is a perspective view of an autoinjector system showing a cassette engaged with an injector in accordance with the present invention.

Referring initially to FIG. 1, an autoinjector system in accordance with the present invention is shown and is generally designated 10. As shown, the system 10 essentially includes a disposable cassette 12 and a re-useable injector 14. Further, as shown in phantom in FIG. 1, a drive assembly 16 and a microcomputer 18 are mounted inside the injector 14. As intended for the present invention, the microcomputer 18 is activated by depression of the button 20 on the injector 14. And, when activated, the microcomputer 18 controls the operation of the drive assembly 16 for its interaction with the cassette 12.

Figure 2:
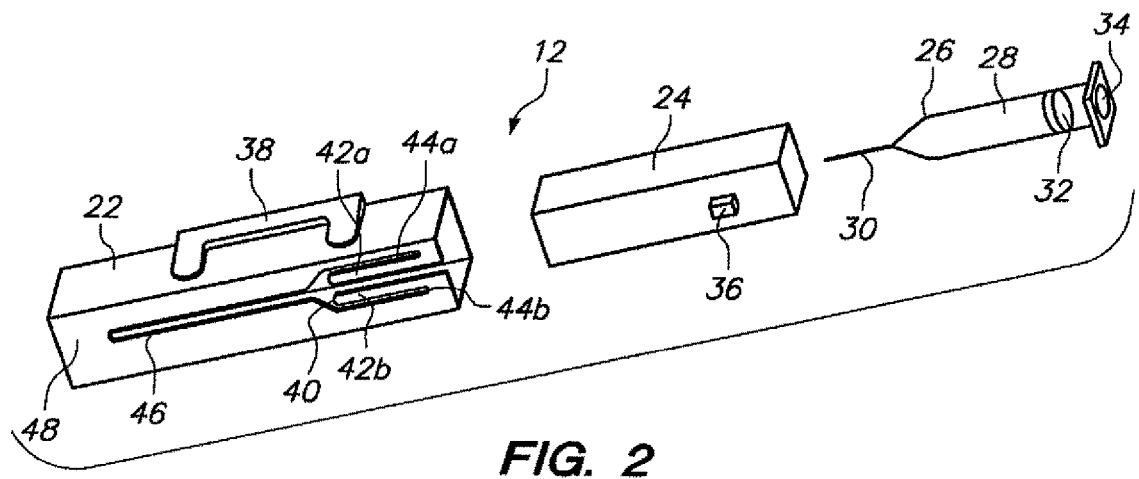
FIG. 2 is an exploded perspective view of the cassette and its component elements for use with the present invention.

In FIG. 2 it will be seen that the cassette 12 includes a housing 22, a sleeve member 24 and a syringe assembly 26. More specifically, the syringe assembly 26 is of a type well-known in the pertinent art that has a syringe chamber 28 for holding a fluid medicament. The syringe assembly 26 will also have an injection needle 30, and a plunger 32 that is moveable within the syringe chamber 28 to expel fluid medicament from the syringe chamber 28 through the injection needle 30. FIG. 2 also shows that the syringe assembly 26 is formed with an orifice 34 that allows for contact with the plunger 32 for the stated purpose. As intended for the present invention, the syringe assembly 26 is fixedly joined with the sleeve member 24 and this combination (i.e. syringe assembly 26 and sleeve member 24) is incorporated with the housing 22 to establish the cassette 12.

Still referring to FIG. 2, it will be seen that the sleeve member 24 includes a protrusion 36. Further, it will be seen that the housing 22 is formed 15 with a fixation member 38 that is dimensioned for engagement with the injector 14 (see FIG. 1). As is to be appreciated by the skilled artisan, the fixation member 38 engages with the injector 14 to position the cassette 12 in an operational alignment with the drive assembly 16. Importantly, the cassette 12 can be fixedly held on the injector 14 during an operation duty cycle of the system 10, and selectively removed from the injector 14 after its use.

FIG. 2 also shows that the housing 22 is formed with a latch mechanism 40. In detail, the latch mechanism 40 includes a pair of opposed, resilient arms 42a and 42b that are respectively formed with a detent 44a and 44b. As shown, the resilient arms 42a and 42b straddle a slot 46 that extends along the side 48 of the housing 22.

An important aspect of the present invention involves the assembly of the cassette 12 into an integral unit. When assembled, it is to be appreciated that the cassette 12 is intended for use only so long as there is fluid medicament in the syringe chamber 28 and, it is thereafter disposable. Prior to assembly, the syringe assembly 26 will have a pre-filled syringe chamber 28 holding a defined dose. The pre-filled syringe assembly 26 is then inserted into the sleeve member 24 where it is fixedly held. Movements of the sleeve member 24 will thus result in a corresponding movement of the syringe assembly 26. The combination (i.e. syringe assembly 26 and sleeve member 24) is then joined with the housing 22. When so joined, the protrusion 36 on 5 sleeve member 24 fits in the detents 44a and 44b between the resilient arms 42a and 42b. Accordingly, the syringe assembly 26 is held on the cassette 12 in a so-called "home position". Importantly, with the syringe assembly 26 in the "home position", the injection needle 30 of the syringe assembly 26 is held, and concealed within the housing 22. In this configuration, the cassette 12 can be engaged with the injector 14 substantially as shown in FIG. 1.

Figure 3A:
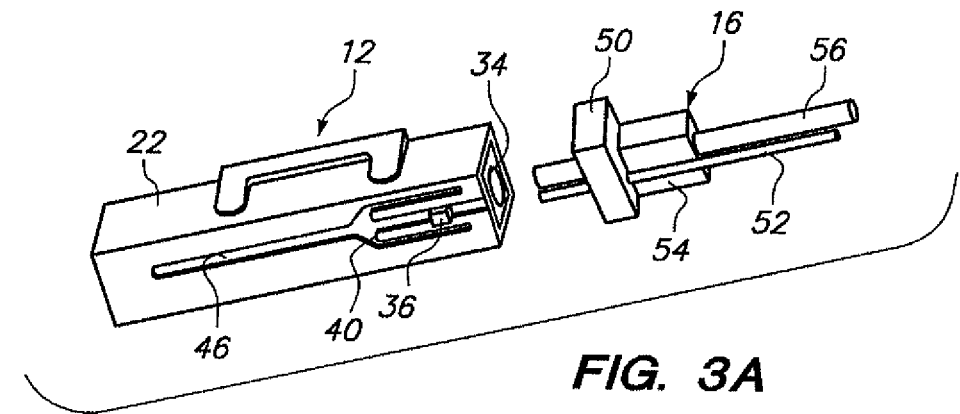
FIG. 3A is a perspective view of a cassette and a drive assembly of the system in position at the beginning and at the end of a duty cycle.
Figure 3B:
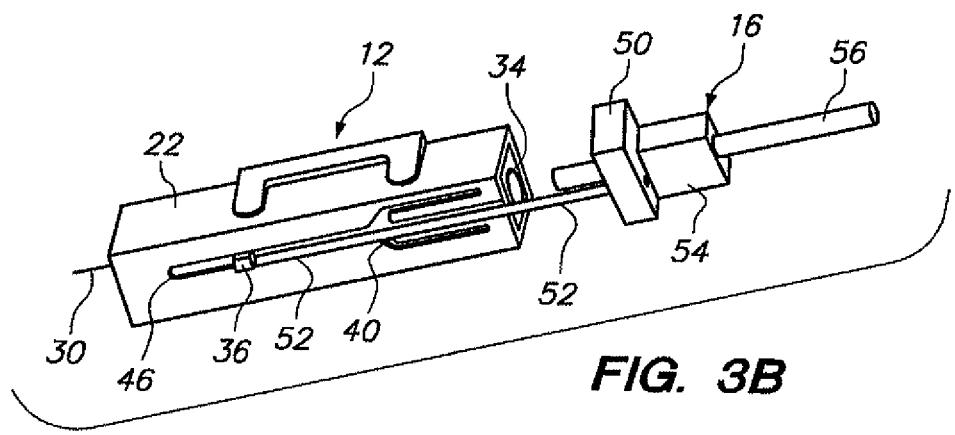
FIG. 3B is a view of the components shown in FIG. 3A with the syringe in the cassette being advanced by a first motor of the drive assembly for insertion of the syringe needle into a patient.
Figure 3C:
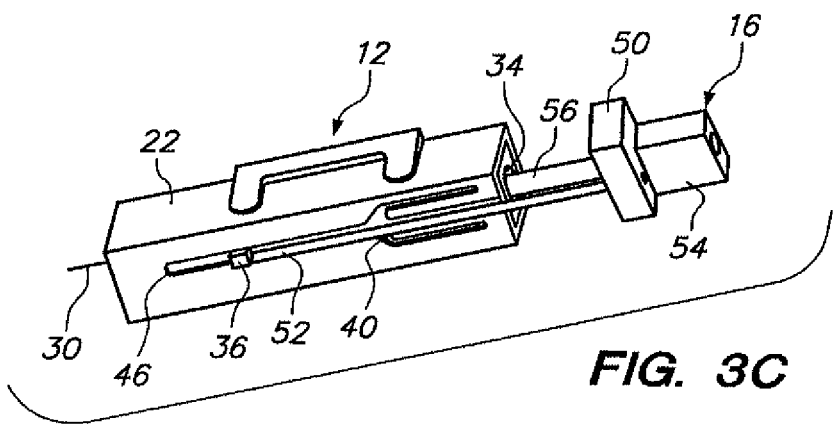
FIG. 3C is a view of the components shown in FIG. 3B with the plunger in the syringe being advanced by a second motor of the drive assembly for injection of a fluid medicament from the syringe into the patient.

For an operation of the system 10, reference is directed collectively to FIGS. 3A, 3B and 3C. Although the injector 14 is not shown in these Figs., it is to be appreciated that the cassette 12 and the drive assembly 16 are to be considered as being operationally mounted on the injector 14 (i.e. cross-reference FIGS. 3A, 3B and 3C with FIG. 1). Further, in greater detail, the drive assembly 16 is shown in FIG. 3A to include a first motor 50 that is used to move a drive rod 52. Also, a second motor 54 is shown that is used to move a pusher 56. For purposes of the present invention, the motors 50 and 54 can be of any type well known in the pertinent art. Furthermore, the respective movements of drive rod 52 and pusher 56 can be provided by any well known mechanical device such as a lead screw or a rackand-pinion. As noted above, the operations of the first motor 50 and the second motor 54 are both controlled by the microcomputer 18.

In overview, a duty cycle for the system 10 can be envisioned as a series of sequential changes in the configuration of cassette 12. For system 10, these configuration changes are caused by separate operations of the first motor 50 and the second motor 54. In compliance with these operations, a complete duty cycle for the system 10 will constitute, in order, configurations shown from FIG. 3A, to FIG. 3B, to FIG. 3C, and then in reverse order from FIG. 3C, back to FIG. 3B and FIG. 3A.

FIG. 3A, shows the cassette 12 with the syringe assembly 26 in its "home position." Importantly, in this "home position" the protrusion 36 on sleeve member 24 is held by the latch mechanism 40 on housing 22. And, consequently, the injection needle 30 of the syringe assembly 26 is held and concealed within the cassette 12. FIG. 3B shows the cassette 12 with the syringe assembly 26 moved into an advanced position wherein the injection needle 30 has been extended from the cassette 12 through a hole 58 at the distal end 60 of the system 10 (see FIG. 1). It is to be appreciated that during the movement from FIG. 3A to FIG. 3B, the first motor 50 advances the drive rod 52. Specifically, with this advancement, the drive rod 52 interacts with latch mechanism 40 to release protrusion 36, and to thereby allow a distal movement of the now "unlatched" syringe assembly 26 and sleeve member 24 on the housing 22. Specifically, this movement is controlled by the microcomputer 18 and is performed with sufficient force to allow the injection needle 30 to penetrate into the tissue of a patient. Preferably, this movement of the syringe assembly 26 from the "home position" (FIG. 3A) to the advanced position (FIG. 3B) is accomplished at a speed of approximately 0.1 to 1 m/s. Further, the first motor 50 can be pre-programmed to stabilize the syringe assembly 26 in its advanced position.

With the syringe assembly 26 in its advanced position (FIG. 3B), microcomputer 18 then activates second motor 54 to move pusher 56 against the plunger 32 in syringe chamber 28 (see FIG. 2). Again, microcomputer 18 is in control and, in this case, can be pre-programmed to advance the plunger 32 at an appropriate speed for injection of the fluid medicament from the syringe chamber 28. At the completion of the injection, the respective configurations of the cassette 12 and the drive assembly 16 are as shown in FIG. 3C. As mentioned above, completion of the injection duty cycle requires the pusher 56 be withdrawn. This withdrawal of the pusher 56 is accomplished by the second motor 54. Once the pusher 56 has been withdrawn (see FIG. 3B), the first motor 50 is again activated to withdraw the drive rod 52. The drive rod 52 then pulls the protrusion 36 back for engagement with the latch mechanism 40, and the syringe assembly 26 is thus returned to its "home position." The cassette 12 can then be removed from the injector 14 and discarded.

As an additional feature of the system 10, a sensor 62 can be provided at the distal end of the injector 14. In particular, the sensor 62 should be positioned adjacent the hole 58 of cassette 12. For purposes of the present invention, the sensor 62 is preferably of a type that will react to capacitance that can be measured between the sensor 62 and the skin of the patient. The purpose of this sensor 62 is to establish that system 10 is in physical contact with the patient. Specifically, the microcomputer 18 will operate a duty cycle for the system 10 only when such contact is indicated. Otherwise, there can be no operation of the system 10.

While the particular System and Method for an Injection Using a Syringe Needle as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A disposable cassette for use with a reusable injector, the cassette comprising:
   a housing;
   a sleeve movable in the housing;
   a hypodermic syringe fixedly held within the sleeve for movement therewith in the housing, the syringe comprising an injection needle and a fluid medicament; and
   a latch mechanism for latching the sleeve within the housing of the disposable cassette, the latch mechanism comprising first and second parts;
   wherein the housing includes one of the first and second parts of the latch mechanism and the sleeve includes the other one of the first and second parts of the latch mechanism;
   wherein the latch mechanism is configured to be unlatched by the reusable injector, thereby allowing the sleeve and the syringe fixedly held within the sleeve, to be moved within the housing by the reusable injector from a first position where the injection needle is concealed within the housing of the disposable cassette, to a second position where the injection needle extends from the housing of the disposable cassette; and
   wherein the latch mechanism is configured to be relatched by the reusable injector when the injector moves the sleeve and the syringe fixedly held within the sleeve, back to the first position where the injection needle is concealed within the housing of the disposable cassette from the second position where the injection needle extends from the disposable cassette.

2. A disposable cassette as recited in claim 1 wherein the housing comprises an orifice for allowing the injection needle to extend from the housing of the disposable cassette in the second position.

3. A disposable cassette as recited in claim 1 wherein the hypodermic syringe further comprises:
   a chamber for holding the fluid medicament, the injection needle extending from the syringe chamber; and
   a plunger slidably disposed within the syringe chamber for expelling the fluid medicament therefrom through the injection needle.

4. A disposable cassette as recited in claim 1 wherein the hypodermic syringe is nonremovably disposed within the housing of the cassette.

5. A disposable cassette as recited in claim 1 wherein the housing includes a detent comprising the one of the first and second parts of the latch mechanism and the sleeve includes a protrusion comprising the other one of the first and second parts of the latch mechanism, and wherein the protrusion is held by the detent when the latch mechanism is latched.

6. A disposable cassette as recited in claim 1 wherein a side of the housing includes opposing resilient arms, each of the arms having a detent, the resilient arms and the detents comprising the one of the first and second parts of the latch mechanism and the sleeve includes a protrusion comprising the other one of the first and second parts of the latch mechanism, and wherein the protrusion is held by the detents when the latch mechanism is latched.

7. A disposable cassette as recited in claim 6 wherein the resilient arms straddle a slot that extends along the side of the housing.

8. A disposable cassette as recited in claim 1 wherein the housing includes a fixation member for engaging the injector to position the cassette in operational alignment with a drive assembly of the injector.

\* \* \* \* \*

UNITED STATES PATENT AND TRADEMARK OFFICE
CERTIFICATE OF CORRECTION

PATENT NO. : 9,616,173 B2  
APPLICATION NO. : 13/269750  
DATED : April 11, 2017  
INVENTOR(S) : John B. Slate et al.

Page 1 of 1

It is certified that error appears in the above-identified patent and that said Letters Patent is hereby corrected as shown below:

On the Title Page

At item (73), "Avant Medical Corporation" should be -- Avant Medical Corp. --.

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*